(12) United States Patent
Demers (10) Patent No.: US 7,439,511 B2
(45) Date of Patent: Oct. 21, 2008

(54) PULSED TERAHERTZ FREQUENCY DOMAIN SPECTROMETER WITH SINGLE MODE-LOCKED LASER AND DISPERSIVE PHASE MODULATOR

(75) Inventor: Joseph R. Demers, Glendale, CA (US)

(73) Assignee: Emcore Corporation, Albuquerque, NM (US)

( * ) Notice: Subject to any disclaimer, the term of this patent is extended or adjusted under 35 U.S.C. 154(b) by 0 days.

(21) Appl. No.: 11/796,069

(22) Filed: Apr. 26, 2007

(65) Prior Publication Data

US 2008/0179528 A1 Jul. 31, 2008

Related U.S. Application Data

(63) Continuation-in-part of application No. 11/669,685, filed on Jan. 31, 2007.

(51) Int. Cl.
*G01J 5/02* (2006.01)
(52) U.S. Cl. .................................... 250/341.1
(58) Field of Classification Search ............... 250/341.1
See application file for complete search history.

(56) References Cited

U.S. PATENT DOCUMENTS

| 5,379,309 | A | 1/1995 | Logan, Jr. |
| 5,623,145 | A | 4/1997 | Nuss |
| 6,304,219 | B1 | 10/2001 | Rothe |
| 6,348,683 | B1 | 2/2002 | Verghese et al. |
| 6,816,647 | B1 | 11/2004 | Rudd et al. |
| 6,811,552 | B2 | 1/2005 | Zhang et al. |
| 6,849,852 | B2 | 2/2005 | Williamson |
| 6,865,014 | B2 | 3/2005 | Ciesla et al. |
| 7,174,037 | B2 | 2/2007 | Amone et al. |
| 2006/0255277 | A1 | 11/2006 | Cole et al. |

OTHER PUBLICATIONS

Takeshi Yasui, Yasuhiro Kabetani, Eisuke Saneyoshi, Shuko Yokoyama, Tsutomu Araki, "Terahertz Frequency Comb by Multifrequency-Heterdyning Photoconductive Detection for High-Accuracy, High Resolution Terahertz Spectroscopy", Applied Physics Letters 88, 241104 (pp. 1-3) (2006), American Institute of Physics.

S. Verghese, K.A. McIntosh, S. Calawa, W.F. Dinatale, E.K. Duerr, K.A. Molvar, "Generation and Detection of Coherent Terahertz Waves Using Two Photomixers", Applied Physics Letters, vol. 73, No. 26, 3824-3826, 1998 American Institute of Physics.

Guoqing Chang, Charles J. Divin, Chi-Hung Liu, Steven L. Williamson, Almantas Galvanauskas, Theodore B. Norris, "Power Scalable Compact THz System Based on an Ultrafast Yb-doped Fiber Amplifier", Optics Express, vol. 14, Issue 17, pp. 7909-7913, Optics InfoBase, The Optical Society of America.

(Continued)

*Primary Examiner*—Constantine Hannaher
*Assistant Examiner*—Marcus H Taningco (57) ABSTRACT

An apparatus for analyzing, identifying or imaging an target including a source of pulsed signals in the range of frequencies from 100 GHz to over 2 THz focused on or transmitted through the target; and a detector for acquiring spectral information from signals reflected from the target and using a multi-spectral heterodyning process to generate an electrical signal representative of some characteristics of the target. The source of pulse signals and the detector are photoconductive switches activated by a pulsed laser beam from a single mode-locked laser.

28 Claims, 7 Drawing Sheets

OTHER PUBLICATIONS

A. Bartels, F. Hudert, C. Janke, T. Dekorsy, K. Kohler, "Femtosecond Time-Resolved Optical Pump-Probe Spectroscopy at Kilo Rates Over Nanosecond-Time-Delays Without Mechanical Delay Line", Applied Physics Letters, 88, 04117 (2006), Scitation Abstract.

A. Bartels, A. Thoma, C. Janke, T. Dekosry, A. Dreyhaupt, S. Winnerl, M. Helm, "High-Resolution THz Spectrometer with kHz Scan Rates", Optics Express, vol. 14, Issue 1, pp. 430-437 (2006), Optics InfoBase, The Optical Society of America.

C. Janke, M. Forst, M. Nagel, H. Kurz, A. Bartels, "Asynchronous Optical Sampling for High-Speed Characterization of Integrated Resonant Terahertz Sensors", Optics Letters, vol. 30, Issue 11, pp. 1405-1407 (2005), Optics InfoBase, The Optical Society of America.

R. Gutierrez (Caltech), "An Electro-Optical Frequency Shifter", NASA's Jet Propulsion Laboratory, Pasadena, CA, www.nasatech.com/Briefs/Sept00/NPO20531.html, pp. 1-2.

Terahertz Measurements of Resonant Planar Antennas Coupled to Low-Temperature-Grown GaAs Photomixers; K.A. McIntosh et al., 1996 American Institute of Physics; pp. 1-4.

Spectroscopic Applications and Frequency Locking of THz Photomixing with Distributed-Bragg-Reflector Diode Lasers In Low-Temperature-Grown GaAs; Pin Chen et al.; 1997 American Institute of Physics; pp. 1601-1603.

Superconductive Hot Electron Mixers with Ultra Wide RF BandWidth for Heterodyne Receiver Applications Up to 3 THz; W. R. McGrath, et al.; Proceedings of the ESA Symposium; pp. 15-17; Apr. 1997.

PULSED TERAHERTZ FREQUENCY DOMAIN SPECTROMETER WITH SINGLE MODE-LOCKED LASER AND DISPERSIVE PHASE MODULATOR

REFERENCE TO RELATED APPLICATIONS

This application is a continuation-in-part of U.S. patent application Ser. No. 11/669,685 filed Jan. 31, 2007.

BACKGROUND OF THE INVENTION

1. Field of the Invention

The invention relates to microwave, millimeter wave and submillimeter wave sources and in particular to a pulsed heterodyne transceiver useful for terahertz spectroscopy.

2. Description of the Related Art

Terahertz devices and systems generally refer to creating and detecting electromagnetic energy between 300 GHz and 3 terahertz (3 THz), or wavelengths from 100 to 1000 microns (0.1 to 1.0 millimeters), and also referred to as the submillimeter or far-infrared region of the electromagnetic spectrum. Terahertz energy can be created, for example, using short-pulsed lasers, heterodyne lasers, electronic diode multipliers, free-electron lasers, and BWOs.

One important application of terahertz systems is THz spectroscopy, and more particularly realized as time domain spectroscopy. In such systems, a sequence of femtosecond pulses from a mode locked laser are focused onto suitable semiconductor material to produce THz radiation. The radiation is directed to the target or sample to be analyzed, and a detector or detector array is used to collect the signal propagated through or reflected from the object. Since such measurements are made in the time domain by collecting the timed sequence of pulses, the signals must then be processed by a Fourier transformation to recover the frequency domain spectral information.

Terahertz spectroscopy presents many new instrumentation and measurement applications since certain compounds and objects can be identified and characterized by a frequency-dependent absorption, dispersion, and reflection of terahertz signals which pass through or are reflected from the compound or object. Some current terahertz systems perform analyses in the time-domain by collecting that transmitted signal propagating through the object and then processing the information contained in those signals by a Fourier transformer to produce a spectral analysis. By scanning every point or "pixel" on that object, either on a focal plane or in successive focal planes at different ranges, it is also possible for such a system to perform imaging of the surface or interior cross-sections or layers of the object. This non-invasive imaging technique is capable of differentiating between different materials, chemical compositions, or molecules in the interior of an object. However, the Fourier transform from the time domain into the frequency domain imposes limitations on the frequency resolution and upon the ability to look at specific frequency windows.

As noted in a review article by Peter H. Siegel in, IEEE Transactions on Microwave Theory and Techniques, Vol. 50, No. 3, 915-917 (March 2002), terahertz time-domain spectroscopy was pioneered by Nuss and others at Bell Laboratories in the mid-1990s (B. B. Hu and M. C. Nuss, "Imaging with terahertz waves," Opt. Lett., vol. 20, no. 16, pp. 1716-1718, Aug. 15, 1995; D. M. Mittleman, R. H. Jacobsen, and M. C. Nuss, "T-ray imaging," IEEE J. Select. Topics Quantum Electron., vol. 2, pp. 679-692, September 1996), and recently commercialized by at least two companies, Picometrix, LLC of Ann Arbor, Mich. (D. D. Arnone et al., "Applications of terahertz (THz) technology to medical imaging," in Proc. SPIE Terahertz Spectroscopy Applicat. II, vol. 3823, Munich, Germany, 1999, pp. 209-219) and Teraview Ltd. (a spinoff of Toshiba Research Europe) located in Cambridge, England (D. Arnone, C. Ciesla, and M. Pepper, "Terahertz imaging comes into view," Phys. World, pp. 35-40, April 2000).

In situ measurements of the transmitted or reflected terahertz energy incident upon a small sample are processed to reveal spectral content (broad signatures only), time of flight data (refractive index determination, amplitude and phase, and sample thickness), and direct signal strength imaging. The principle involves generating and then detecting terahertz electromagnetic transients that are produced in a photoconductor or a crystal by intense femtosecond optical laser pulses. The laser pulses are beam split and synchronized through a scanning optical delay line and made to strike the terahertz generator and detector in known phase coherence. By scanning the delay line and simultaneously gating or sampling the terahertz signals incident on the detector, a time-dependent waveform proportional to the terahertz field amplitude and containing the frequency response of the sample is produced. Scanning either the terahertz generator or the sample itself allows a 2-D image to be built up over time.

Other developments include rapid scanning (S. Hunsche and M. C. Nuss, "Terahertz 'T-ray' tomography," in Proc. SPIE Int. Millimeter Submillimeter Waves Applicat. IV Conf., San Diego, Calif., July 1998, pp. 426-433.) and true 2-D sampling using charge-coupled device (CCD) arrays (Z. Jiang and X.-C. Zhang, "Terahertz imaging via electrooptic effect," IEEE Trans. Microwave Theory Tech., vol. 47, pp. 2644-2650, December 1999.). In the Picometrix and Lucent Technologies systems, the generator and detector are based on the photoconductive effect in low-temperature-grown (LTG) GaAs or radiation-damaged silicon on sapphire semiconductor. The Teraview system uses terahertz generation by difference frequency mixing in a nonlinear crystal (ZnTe) and detection via the electrooptical Pockels effect (measuring the change in birefringence of ZnTe induced by terahertz fields in the presence of an optical pulse) as first demonstrated by Zhang at the Rensselaer Polytechnic Institute (RPI), Troy, N.Y. (see Q. Wu, T. D. Hewitt, and X.-C. Zhang, "Two-dimensional electro-optic imaging of THz beams," Appl. Phys. Lett., vol. 69, no. 8, pp. 1026-1028, Aug. 19, 1996.). The femtosecond optical pulses are currently derived from relatively expensive Ti: Sapphire lasers, but other proposals include longer wavelength, especially 1.5 m, solid-state systems that can take better advantage of fiber technology (see D. M. Mittleman, R. H. Jacobsen, and M. C. Nuss, "T-ray imaging," IEEE J. Select. Topics Quantum Electron., vol. 2, pp. 679-692, September 1996). The RF signals produced by the optical pulses typically peak in the 0.5-2 THz range and have average power levels in the microwatt range and peak energies around a femtojoule. This makes T-ray imaging an attractive tool for medical applications (noninvasive sampling), as well as for nondestructive analysis of biological materials or electronic parts. The largest drawback of prior art designs is the need to scan the delay line slowly and over a distance of the desired wavelength resolution (e.g., a 1 GHz resolution would require a 7.5 cm scan) and the inability to look at discrete frequencies of interest.

The need for a multi-octave tunable spectrometer in the THz region is justified by the new suite of applications relating to materials identification facing researchers and system developers today. Historically, the THz field has been dominated by radio astronomers and chemists usually aimed at detecting trace amounts of small gaseous molecules in the interstellar medium or in the Earth's upper atmosphere. The low pressure of the media involved would often lead to narrow, Doppler-limited absorption lines, sometimes less than 1 MHz in linewidth. In roughly the last decade, the THz landscape has changed dramatically with the discovery and demand for detection and imaging of larger molecules, particularly biomolecules and bioparticles. This includes, for example, proteins and vitamins using frequency sweeps above 1 THz, and bacterial spores and nucleic acids using frequency sweeps below 1 THz. In all cases the biomolecular and bioparticle absorption occurs not in the form of narrow lines, but rather as broad "signatures", typically 1 to 10 GHz or wider. A good example of a bioparticle of current research interest would be the spores of *Bacillus subtilis* (an Anthrax surrogate), which have recently displayed approximately 6 GHz broad signatures centered around 260 and 420 GHz. In addition, these signatures tend to have less maximum absorption strength than their small molecular counterparts, making them more difficult to "specify" against background noise, standing waves, and other spurious effects. A multi-octave spectrometer capable of measuring small discrete windows of frequencies allows measurement of two or more signatures in the same session, increasing confidence and specificity.

In addition to the time-domain spectrometers noted above, frequency domain systems are also known (See the paper by Verghese et al., "Generation and detection of coherent terahertz waves using two photomixers," Appl. Phys. Lett., vol. 73, no. 26, pp. 3824-3826, Dec. 28, 1998.). One prior art terahertz spectrometer system is described in U.S. patent application Ser. No. 11/121,350, assigned to the common assignee, and hereby incorporated by reference. The system includes a laser illumination arrangement that generates a pair of source laser beams incident on a source photomixer device or photoconductive switch (PCS) to cause emission of subcentimeter radiation, at least a portion of which interacts with the remote sample to generate a "sample influenced radiation" which is then incident on a detector photomixer device. A second pair of laser beams is incident on the detector to produce an optical component of the detector photocurrent that is offset in frequency with respect to the detected source laser energy. As a result, the detector generates a frequency down-converted electrical output signal responsive to and characteristic of the sample influenced radiation.

SUMMARY OF THE INVENTION

1. Objects of the Invention

It is an object of the present invention to provide an improved frequency domain terahertz spectrometer using a single mode locked laser.

It is another object of the present invention to provide a terahertz pulse comb system for the identification of a target spectrum.

It is also another object of the present invention to provide a multi spectrum heterodyne receiver for a terahertz system utilizing a single mode locked laser.

It is still another object of the present invention to provide a field portable terahertz system utilizing a single mode locked laser capable of identifying or imaging an object.

2. Features of the Invention

Briefly, and in general terms, the present invention provides an apparatus for analyzing, identifying or imaging a target (such as the atmosphere, or a material substance such as a chemical compound or object), including a source of pulse signals in the range of frequencies from 100 GHz to over 2 THz including a first photoconductive switch activated by a pulsed optical beam from a laser resulting in a frequency spectrum f, 2f, 3f, . . . etc. where f is the order of 100 MHz, directing means for causing the signals to be substantially simultaneously focused on the compound or object or simultaneously transmitted through the compound or object, and a detector for acquiring spectral information reflected from or transmitted through the compound or object and coupled to a second pulsed optical beam derived from the laser for generating an electrical signal representative of some characteristic of the compound or object.

In another aspect, the present invention provides an apparatus for analyzing, identifying or imaging a target, including a source of pulse signals in the range of frequencies from 100 GHz to over 2 THz, directing means for causing the signals to be substantially simultaneously focused on the compound or object or simultaneously transmitted through the compound or object, a detector including a photoconductive switch activated by a pulsed laser beam with the frequency spectrum $f+\Delta f, 2(f+\Delta f), 3(f+\Delta f), \ldots$ etc. where f is the order of 100 MHz and $\Delta f$ is of the order of 2.5 KHz, for acquiring spectral information reflected from or transmitted through the compound or the object for generating an electrical signal representative of some characteristics of the compound or the object, and means coupled to the detector for processing the electrical signal.

In another aspect, the present invention provides a portable apparatus for analyzing, identifying or imaging a target, including a housing capable of being supported by a user, a source of pulse signals in the housing including a single mode-locked laser, the signals being in the range of frequencies from 100 GHz to over 2 THz, directing means in the housing for causing the signals to be focused on the target or simultaneously transmitted through the target, a detector in the housing for acquiring spectral information reflected from or transmitted through the target and generating an electrical signal representative of some characteristics of the compound or object; and means in the housing coupled to the detector for processing the electrical signal.

In another aspect, the present invention provides a transceiver including a mode-locked laser for generating a pulsed laser beam, a beam splitter for splitting the beam into first and second optical beams, a photoconductive switch activated by the first optical beam resulting in a frequency spectrum f, 2f, 3f, . . . etc. where f is the order of 100 MHz, and a detector including a photoconductive switch activated by the second optical beam with the frequency spectrum $f+\Delta f, 2(f+\Delta t), 3(f+\Delta f), \ldots$ etc. where $\Delta f$ is of the order of 2.5 KHz, for acquiring spectral information reflected from or transmitted through the target and coupled to source for generating an electrical signal representative of some characteristics of the target.

In another aspect, the present invention provides a method of identifying or imaging a target including the steps of providing a single mode-locked laser for generating a pulsed laser beam, simultaneously transmitting a predetermined spectral pattern of pulse signals derived from the pulsed laser beam to an object, the signals being in the range of frequencies from 100 GHz to over 2 THz, detecting the transmitted or returned signals in the frequency range after propagation through or reflection from the object by utilizing a detector tuned to the spectral pattern derived from the pulsed laser beam shifted by a sequence of non-identical small amounts from the spectral pattern, and analyzing the spectral information to identify the target or constituents thereof.

Additional objects, advantages, and novel features of the present invention will become apparent to those skilled in the art from this disclosure, including the following detailed description as well as by practice of the invention. While the invention is described below with reference to preferred embodiments, it should be understood that the invention is not limited thereto. Those of ordinary skill in the art having access to the teachings herein will recognize additional applications modifications and embodiments in other fields, which are within the scope of the invention as disclosed and claimed herein and with respect to which the invention could be of utility.

BRIEF DESCRIPTION OF THE DRAWINGS

These and other features and advantages of this invention will be better understood and more fully appreciated by reference to the following detailed description when considered in conjunction with the accompanying drawings wherein.

The novel features and characteristics of the invention are set forth in the appended claims. The invention itself, however, as well as other features and advantages thereof, will be best understood by reference to a detailed description of a specific embodiment, when read in conjunction with the accompanying drawings.

DETAILED DESCRIPTION OF THE PREFERRED EMBODIMENT

Details of the present invention will now be described, including exemplary aspects and embodiments thereof. Referring to the drawings and the following description, like reference numbers are used to identify like or functionally similar elements, and are intended to illustrate major features of exemplary embodiments in a highly simplified diagrammatic manner. Moreover, the drawings are not intended to depict every feature of actual embodiments or the relative dimensions of the depicted elements, and are not drawn to scale.

Figure 1A:
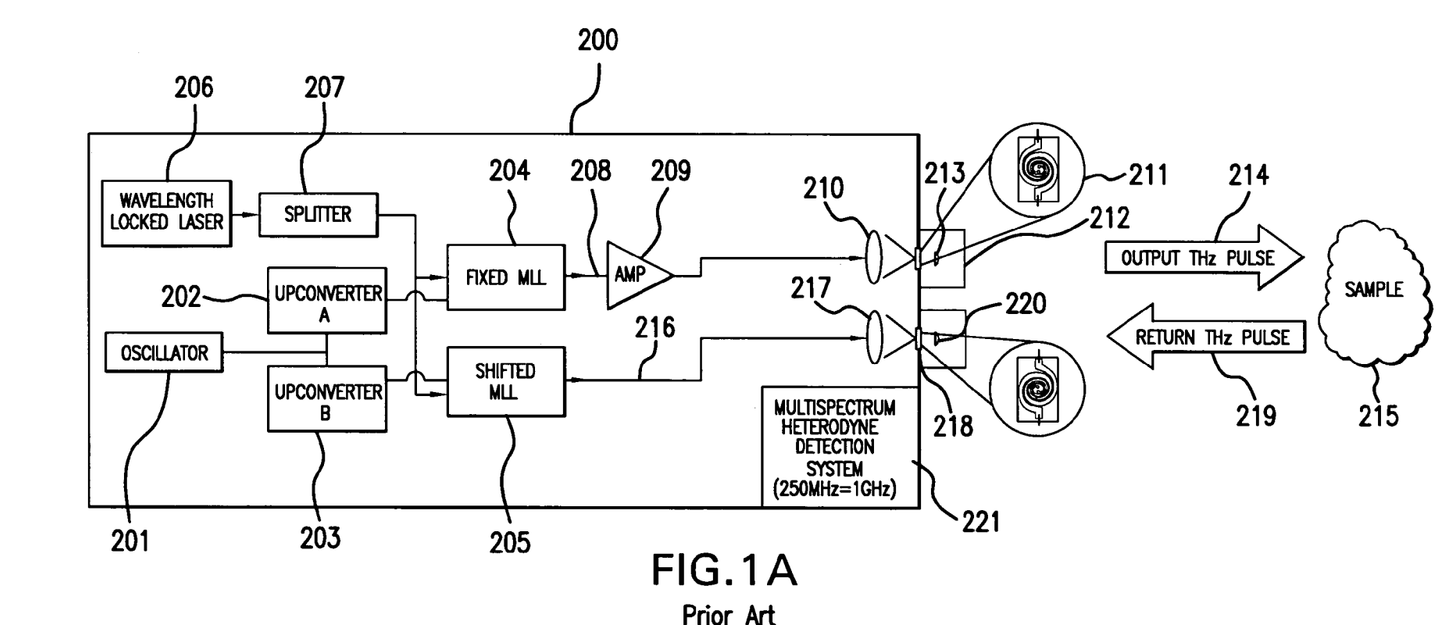
FIG. 1A is a block diagram of a frequency domain terahertz spectrometer known in the prior art which employs reflection from the sample.
Figure 1B:
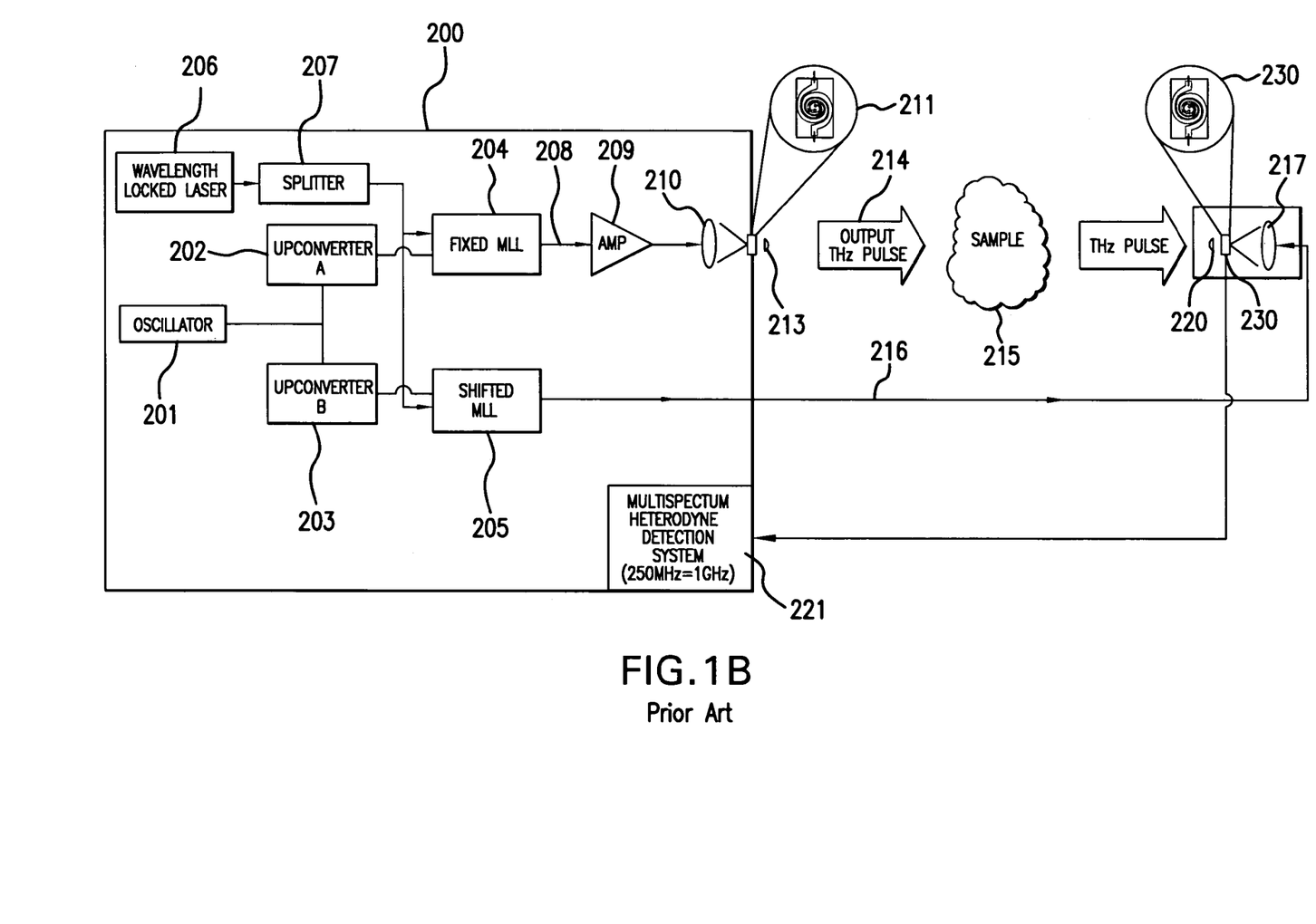
FIG. 1B is a block diagram of a frequency domain terahertz spectrometer known in the prior art which employs transmission through the sample.

FIGS. 1A and 1B depict frequency domain terahertz spectrometers known in the prior art. A prior art spectrometer as described in U.S. patent application Ser. No. 11/669,685, is depicted in the block diagram of FIG. 1A, which employs reflection from the sample, while FIG. 1B depicts a similar prior art spectrometer that employs transmission through the sample.

The FIGS. 1A and 1B show the spectrometer disposed in a housing 200, suited for portable use in the field. A crystal oscillator 201 produces a 1 KHz pulse which drives two upconverters 202 and 203 whose output is applied to a pair of mode locked lasers 204 and 205. The output of upconverter 202 is 100 MHz, and the output of upconverter 203 is 100.0025 MHz. The mode locked lasers are preferably 780 nm lasers of Calmar Optcom Inc. of Sunnyvale, Calif. The output of laser 204 is a comb of equally spaced pulses centered at 100 MHz, 200 MHz, 300 MHz, . . . 1000 GHz, 1000.100 GHz, etc. The output of laser 205 is a comb of equally spaced pulses at 100.0025 MHz, 200.005 MHz, 300.0075 MHz, . . . 1000.0025 GHz, 1000.1250025 GHz, etc. The lasers 204 and 205 may be driven by a wavelength locked laser 206, whose output is applied to a beam splitter 207, producing separate beams applied to lasers 204 and 205 respectively.

The output 208 of laser 204 is amplified by an optical amplifier 209, and the beam is in turn applied to a lens 210 which focuses the beam to a ten micron spot on the surface of a low temperature grown (LTG) gallium arsenide photoconductive switch (PCS) 211. The frequency comb of optical pulses directed to the surface of the PCS semiconductor device produces terahertz radiation in the frequency range 100 GHz to over 2 THz. The terahertz frequency comb spectrum has a fundamental frequency $f_1$ and a series of harmonic components $2f_1, 3f_1, \ldots nf_1 \ldots$ which are integral multiples of the fundamental mode-locked frequency.

The terahertz radiation emitted from the PCS device 211 is collimated and collected by a silicon lens 213, preferably a hemispherically shaped structure approximately one centimeter in diameter. Additional lenses or other elements (represented generically as the attached unit 212), composed of Teflon may be placed downstream of the lens 213 to collimate the RF beams into the output THz pulse 214. Beam-shaping mirrors may also be used in lieu of or in addition to the silicon lens 213.

The target or object 215 to be identified will absorb and transmit some radiation, and also reflect a portion of the radiation back in the direction of the source or user, as shown by the return THz pulse 219. FIG. 1A depicts a prior art embodiment that utilizes the reflected radiation, while FIG. 1B utilizes transmitted radiation.

The output of the shifted mode-locked laser 205 is represented by beam 216 which is directed to a lens 217 which focuses the beam to a ten micron spot on the surface of a LTG GaAs PCS 218 with a design similar to PCS 211, except the spiral arms are in the opposite direction, which acts as the detector. On the receiver side, the return signal 219 and the beam 216 are combined in the LTG GaAs PCS detector 218 to yield a heterodyne signal. This may be described as instantaneous multi-spectral heterodyne down conversion of the return signal. This frequency difference changes from a minimum of 2.5 KHz to a maximum of N times 2.5 KHz, where N is the number of locked modes, and typically the value of N may extend from N=1000 to N=20,000. Due to the extremely wide optical bandwidths of the laser gain media, it is not uncommon for mode-locked lasers to have hundreds of locked modes spanning more than 1000 GHz. Therefore it is possible to generate intensity modulation signals over this wide range of frequencies using the technique according to the present invention. The electrical output of the LTG GaAs detector 218 is in the form of electronic RF signals, which in the case of a spectrometer is processed in generically labeled block 221 in the unit 200 to analyze the data and thereby identify the object or a compositional characteristic thereof, such as the identity of the chemical compounds or material structures contained in the target or object.

In the FIG. 1B embodiment, the components are the same as in the FIG. 1A embodiment, so the above description of FIG. 1A need not be repeated. In the FIG. 1B embodiment, but the placement of the detector PCS 230 is configured so that it is located on the other side of the sample 215 so that the terahertz radiation 214 is transmitted through the sample 215 before being received by the detector PCS 230. Another difference is that the direction of the spiral arms of the PCS 230 is oriented in the same direction as that of PCS 211.

Figure 2A:
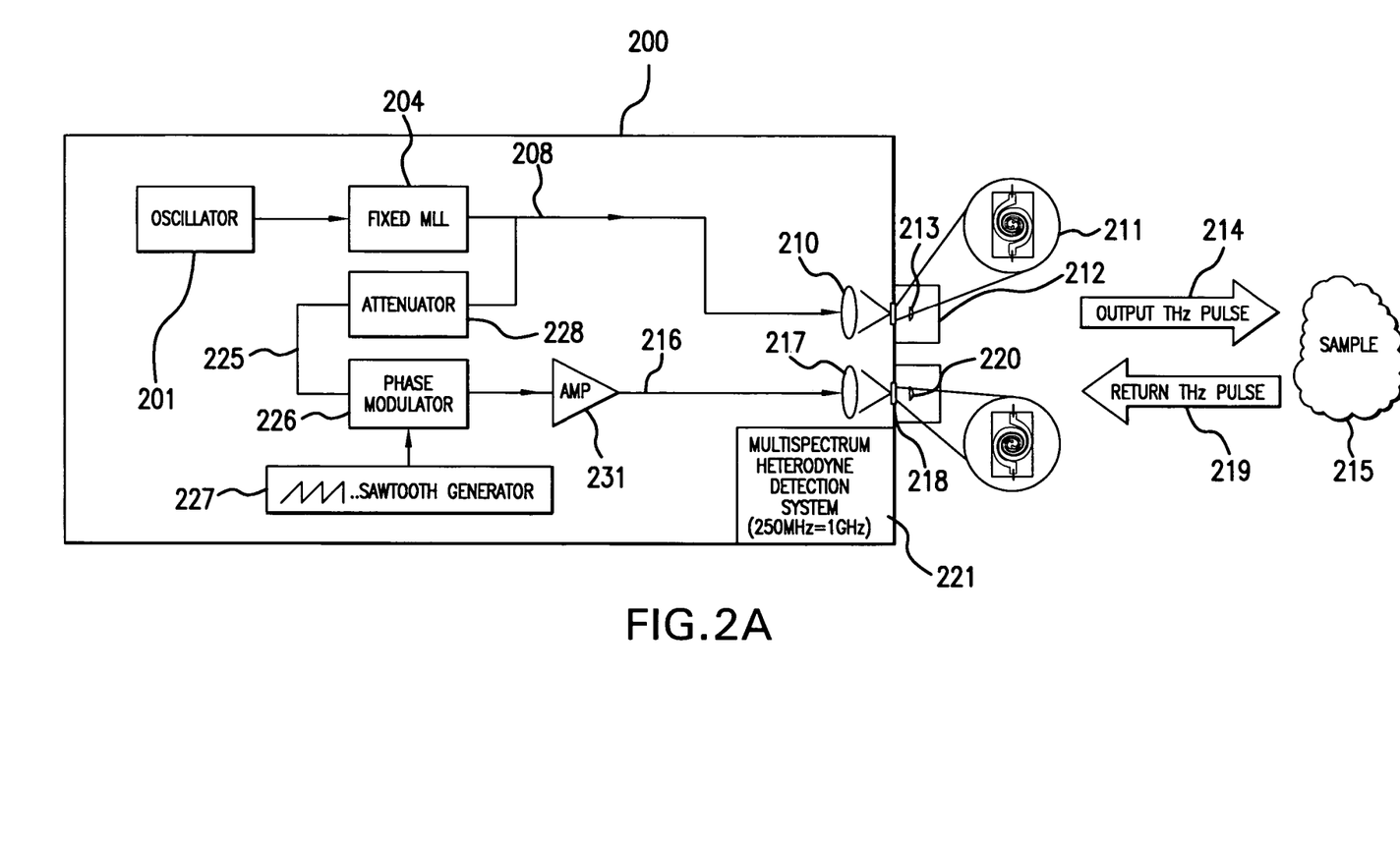
FIG. 2A is a block diagram of a terahertz spectrometer according to the present invention which employs reflection from the sample.
Figure 2B:
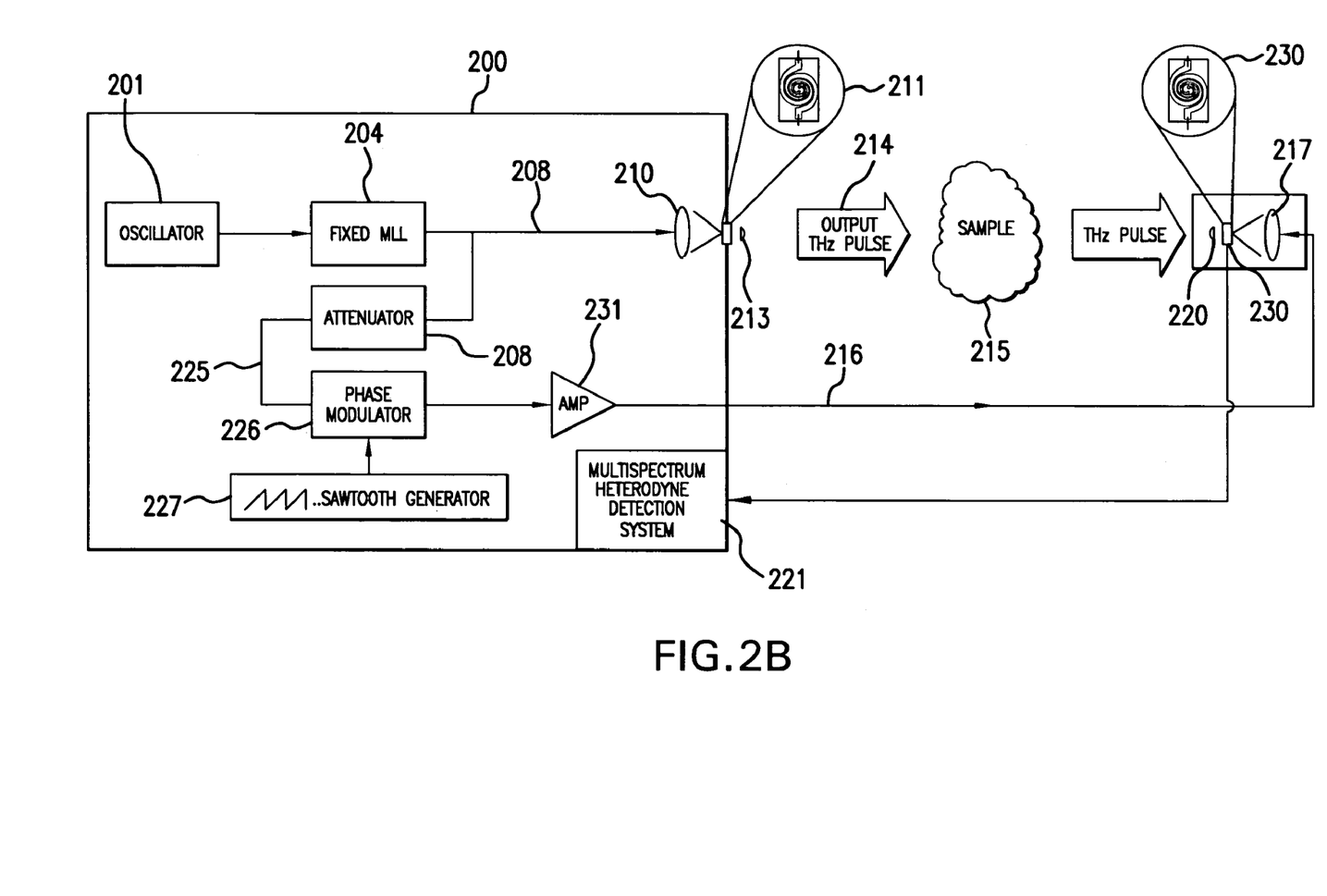
FIG. 2B is a block diagram of a terahertz spectrometer according to the present invention which employs transmission through the sample.

The transceiver or spectrometer of the present invention is depicted in the block diagrams of FIGS. 2A and 2B, which employ reflection or transmission, respectively, through the target or sample. By "transceiver" we mean the embodiment of an electro-optical subassembly, while the spectrometer embodiment incorporates a processor and other electronics for determining the identity or composition of the target, and printing or displaying the results so that the information is readily available to the user.

Figure 3A:
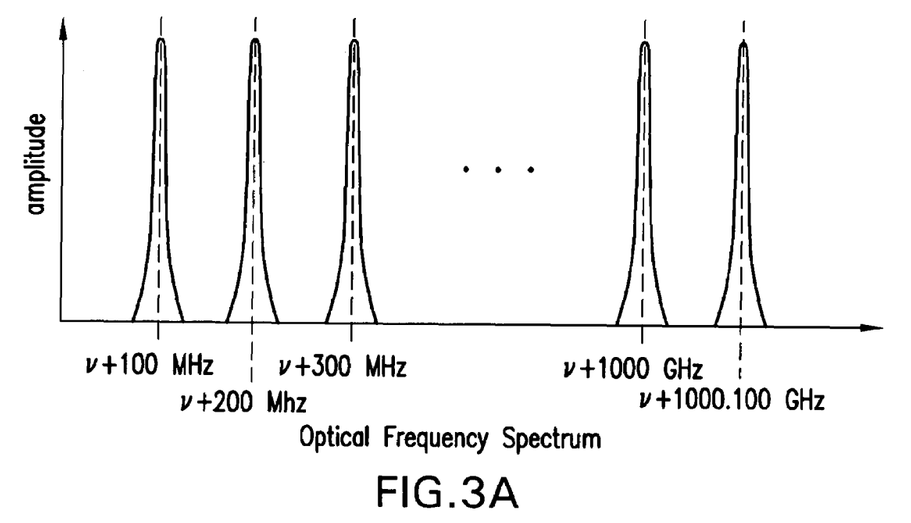
FIG. 3A is a graph illustrating the optical frequency spectrum obtained upon high-speed photodetection of the mode-locked laser in the spectrometer of FIG. 2.

FIGS. 2A and 2B depict a housing 200, suited for portable use of the spectrometer in the field. A crystal oscillator 201 is disposed in the housing that produces a 10 MHz sine wave which drives a single mode-locked laser 204. In the preferred embodiment, the output of the oscillator is 100 MHz. The mode locked laser 204 is preferably a 780 nm laser of Calmar Optcom Inc. of Sunnyvale, Calif. The optical spectrum of the output of laser 204 is depicted in FIG. 3A, which depicts a comb of equally spaced frequency components offset from the optical reference frequency ν by 100 MHz, 200 MHz, 300 MHz, ... 1000 GHz, 1000.100 GHz, etc. substantially similar to the prior art.

In the present invention, the output of the laser 204 is split into two paths, the first path 208 is coupled to the first photoconductive switch 211, and the second path 225 is coupled to an attenuator 228, and then to a beam modifying component 226. The optical propagation path downstream of the laser and throughout the unit 200 may be either free space or an appropriate single-mode polarization maintaining optical fiber.

The output 208 along the first path of laser 204 is applied to a lens 210 which focuses the beam to a spot of approximately ten microns in diameter on the surface of a low temperature grown gallium arsenide photoconductive switch 211. The optical frequency comb signal directed to the surface of the PCS semiconductor device produces terahertz radiation in the frequency range 100 GHz to over 2 THz. The terahertz frequency comb spectrum has a fundamental frequency $f_1$ and a series of harmonic components $2f_1, 3f_1, \ldots nf_1 \ldots$ which are integral multiples of the fundamental mode-locked frequency, as depicted in FIG. 3C.

The terahertz radiation emitted from the PCS device 211 is collimated and collected by a silicon lens 213, preferably a hemispherically shaped structure approximately two to three centimeters in diameter. Additional lenses (not shown), composed of Teflon may be placed downstream of the lens 213 to collimate the RF beams into the output THz pulse 214. Beam-shaping mirrors may also be used in lieu of or in addition to the silicon lens 213.

The target or object 215 to be identified will absorb and transmit some radiation, and also reflect a portion of the radiation back in the direction of the source or user, as shown by the return THz pulse 219. For the purpose of the subsequent discussion, we assume that the target 215 has an absorption spectrum upon transmission or reflection as depicted by the dashed line 300 extending over the terahertz frequency spectrum in FIGS. 3C, 3D, and 3E.

In the present invention, as contrasted with the prior art of FIGS. 1A and 1B, only a single mode-locked laser 204 is needed. The frequency shifted second laser beam provided by the second laser used in the prior art example (i.e., laser 205 in FIG. 1A) may be generated by a beam modifying component, embodied as phase modulator 226 in the present invention. It is known in the prior art, such as described in NASA Technical Brief NPO-20351, to produce a constant frequency shift in an optical signal by exploiting the phase shift of the laser beam as it passes through an electro-optical medium. The effect upon optical frequency of a steadily increasing or decreasing phase shift is equivalent to the Doppler frequency shift produced by a steadily advancing or retreating mirror in the beam path. Of course, there is no practical or physical way to realize, in a compact apparatus, a steadily advancing or retreating mirror. Similarly, there is no practical way to realize its functional equivalent in a phase modulator in which the phase shift could be made to increase or decrease steadily without limit.

However, in the present invention the beam modifying component 226 may be realized by a simple phase modulator 226 employed with a sawtooth wave drive signal 227. A dual phase shifter as described in the NASA paper is not necessary. Data acquisition is timed so that data is only collected during the constantly increasing phase shift. During the moments when the phase modulator is resetting, data acquisition is stopped.

It is not enough to just offset all of the frequency components from the mode locked laser by a constant shift. Such an offset will result in an output with the same repetition rate as the original laser, and will therefore have frequency components that are exactly the same as the source mode locked laser (i.e. they would all be offset an equal amount in the optical domain). For this reason, the phase modulator 226 must be dispersive. That way, the shift of each frequency component (during the ramping of the phase modulator voltage) will be different. If possible, it would be best if this dispersion were increasing with the optical frequency, either in a linear or non-linear manner. During the ramping of the phase modulator voltage, the resulting output would have a different repetition rate that is offset by some constant amount. This would effectively be the same as having a second mode-locked laser 205 as described in parent application Ser. No. 11/669,685.

In the case of a fiber coupled optical system, a dispersive phase modulator 226 may be realized by one of two methods: custom design of a dispersive lithium niobate waveguide or by adjusting the pulse intensity to adjust the induced dispersion in the non-linear lithium niobate. In practice, a combination of these two factors will most likely be required. Since the intensity of the input pulse will need to be varied, it is also likely that post phase modulator amplification will be required as depicted by the inclusion of an optical amplifier 231 in the path of the output of the phase modulator 226. The output 216 of the amplifier 231 is then applied to the lens 217, and then to the PCS 218 detector, which functions in substantially the same manner as the detector 218 in FIG. 1A. The multi-spectral downconversion of the return THz signal 219 is substantially similar to that of FIG. 1A.

The output of amplifier 231 is the beam 216 which is directed to a lens 217 which focuses the beam to a ten micron spot on the surface of a LTG GaAs PCS 218 similar to 211 which acts as the detector. On the receiver side, the return signal 219 and the output 216 of the phase modulator 226 are combined in the LTG GaAs PCS detector 218 to yield a heterodyne signal. This frequency difference changes from a minimum of 2.5 KHz to a maximum of N times 2.5 KHz, where N is the number of locked modes, and typically the value of N may extend from N=1000 to N=20,000. Due to the extremely wide optical bandwidths of the laser gain media, it is not uncommon for mode-locked lasers to have hundreds of locked modes spanning more than 1000 GHz. Therefore it is possible to generate intensity modulation signals over this wide range of frequencies using the technique according to the present invention. The electrical output of the LTG GaAs detector 218 is in the form of electronic RF signals.

Another embodiment of the spectrometer of the present invention is the transmission version depicted in FIG. 2B. In the FIG. 2B embodiment, the components are the same as in the FIG. 2A embodiment, but the placement of the detector PCS 230 is configured so that it is located on the other side of the sample 215 so that the terahertz radiation 214 is transmitted through the sample 215 before being received by the detector PCS 230. Another difference is that the direction of the spiral arms of the PCS 230 is oriented in the same direction as that of PCS 211, as shown in the enlarged top plane views of 211 and 230 shown in FIG. 2B.

Figure 3B:
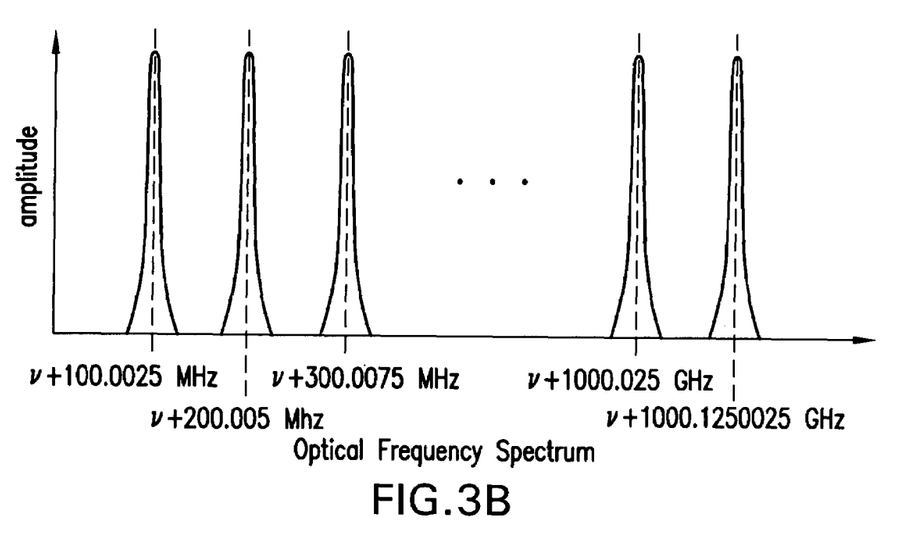
FIG. 3B is a graph illustrating the optical frequency spectrum obtained upon high-speed photodetection of the output of the dispersive phase modulator in the spectrometer of FIG. 2.
Figure 3C:
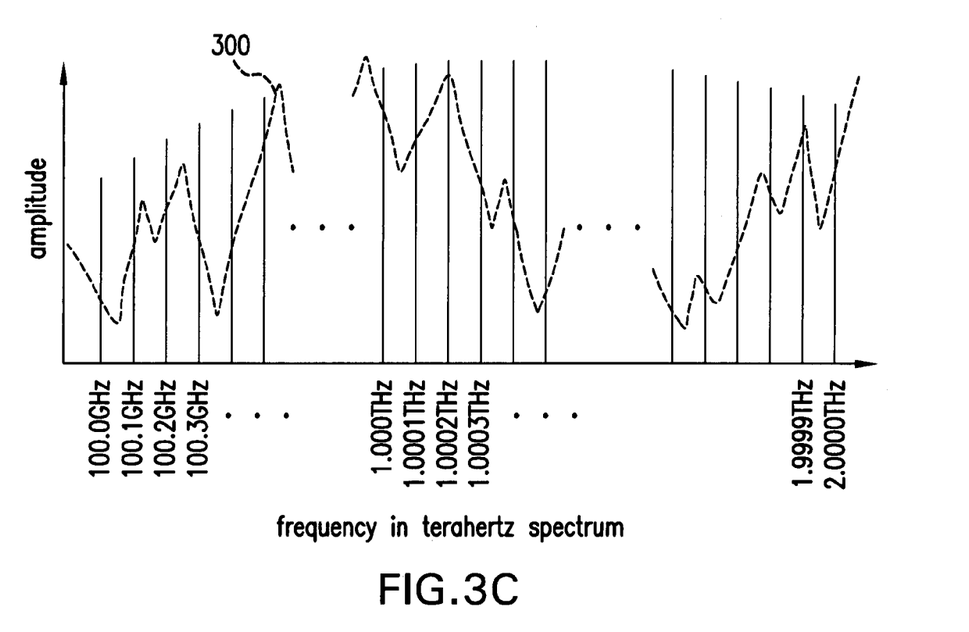
FIG. 3C is a graph illustrating the absorption spectrum of a sample plotted over the frequency spectra of the emitted terahertz RF beam from the photoconductive switch according to the present invention.

The optical spectrum of the output of phase modulator 226 is depicted in FIG. 3B, which depicts a comb of equally spaced frequency components at $\nu+100.0025$ MHz, $\nu+200.005$ MHz, $\nu+300.0075$ MHz, ... $\nu+1000.0025$ GHz, $\nu+1000.1250025$ GHz, etc., where $\nu$ is the optical reference frequency.

Figure 3D:
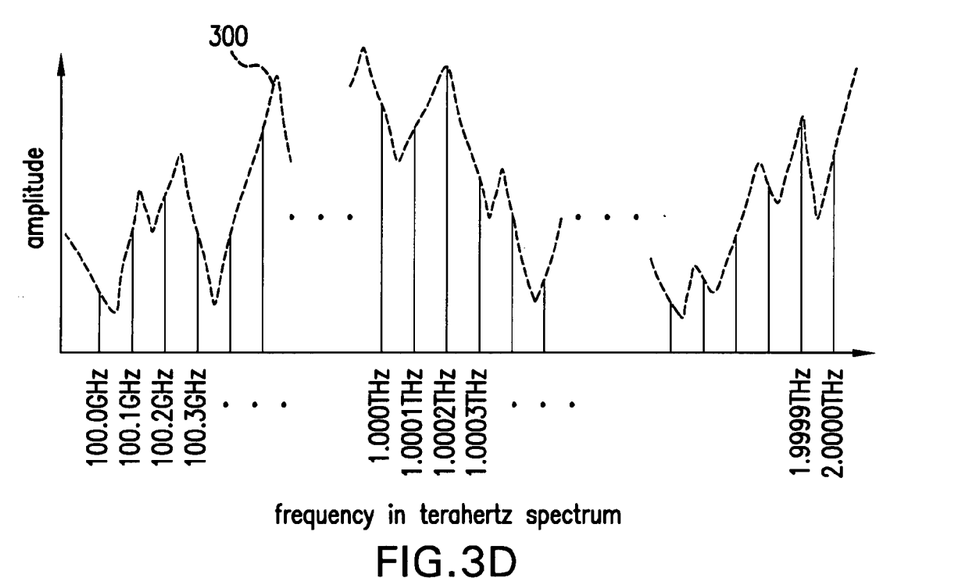
FIG. 3D is a graph illustrating the frequency spectra of the received terahertz RF beam at the detector photoconductive switch according to the present invention.

FIG. 3D is a graph illustrating the frequency spectra of the received terahertz RF beam at the detector photoconductive switch according to the present invention reflected from the target 215. It is noted that the return terahertz signal has been attenuated corresponding to the absorption spectrum 300 of the target, thereby providing a terahertz "signature" which may be used to identify the composition of the target.

Figure 3E:
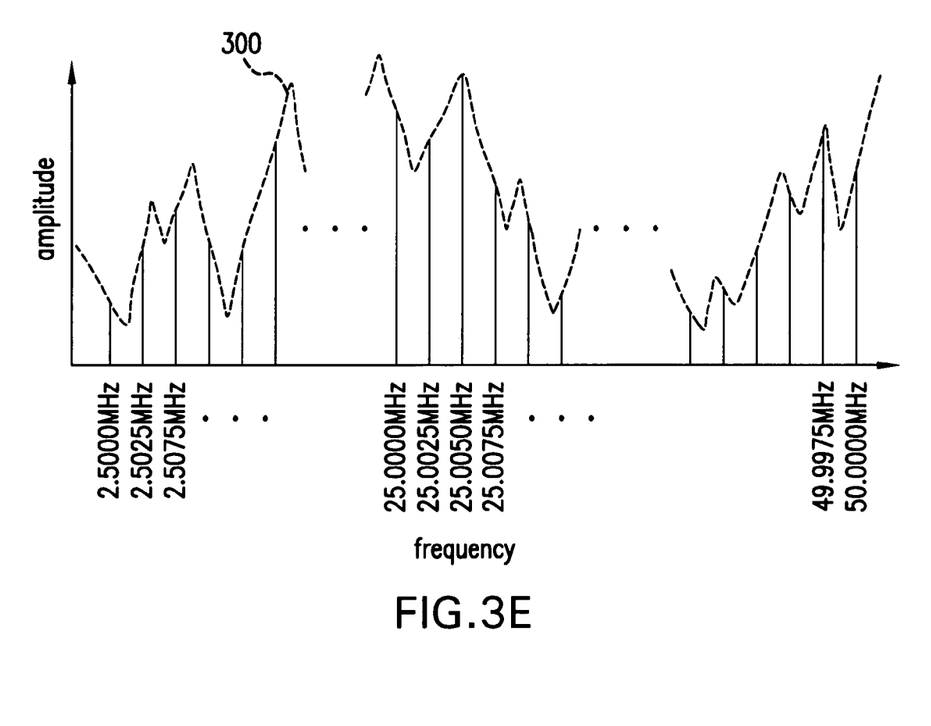
FIG. 3E is a graph illustrating the downconverted spectra in the RF domain.

FIG. 3E is a graph illustrating the downconverted spectra in the RF domain which represents the electrical signal output of the PCS detector 218. The downconverted signal may then be amplified, applied to an analog-to-digital converter, and processed digitally to produce a spectral display or analysis to identify the target or its chemical constituents, as discussed in the prior art references.

Various modifications and improvements of the present invention may also be apparent to those of ordinary skill in the art. Thus, the particular combination of parts described and illustrated herein is intended to represent only certain embodiments of the present invention, and is not intended to serve as limitations of alternate devices within the spirit and scope of the invention.

Various aspects of the techniques and signal processing apparatus of the present invention may be implemented in digital circuitry, or in computer hardware, firmware, software, or in combinations of them. Circuits of the invention may be implemented in computer products tangibly embodied in a machine-readable storage device for execution by a programmable processor, or on software located at a network node or web site which may be downloaded to the computer product automatically or on demand. The foregoing techniques may be performed by, for example, a single central processor, a multiprocessor, one or more digital signal processors, gate arrays of logic gates, or hardwired logic circuits for executing a sequence of signals or program of instructions to perform functions of the invention by operating on input data and generating output. The methods may advantageously be implemented in one or more computer programs that are executable on a programmable system including at least one programmable processor coupled to receive data and instructions from, and to transmit data and instructions to, a data storage system, at least one in/out device, and at least one output device. Each computer program may be implemented in a high-level procedural or object-oriented programming language, or in assembly or machine language if desired; and in any case, the language may be compiled or interpreted language. Suitable processors include, by way of example, both general and special purpose microprocessors. Generally, a processor will receive instructions and data from read-only memory and/or random access memory. Storage devices suitable for tangibly embodying computer program instructions and data include all forms of non-volatile memory, including by way of example, semiconductor devices, such as EPROM, EEPROM, and flash memory devices; magnetic disks such as internal hard disks and removable disks; magneto-optical disks; and CD-ROM disks. Any of the foregoing may be supplemented by or incorporated in, specially designed application-specific integrated circuits (ASICS).

It will be understood that each of the elements described above, or two or more together, also may find a useful application in other types of constructions differing from the types described above.

While the invention has been illustrated and described as embodied in terahertz transceiver or spectrometer system, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed is:

1. An apparatus for analyzing, identifying or imaging a target, comprising:
    a source of pulse signals in the range of frequencies from 100 GHz to over 2 THz including a first photoconductive switch activated by a pulsed optical beam from a laser resulting in a frequency spectrum f, 2f, 3f, ... etc. where f is the order of 100 MHz;
    a radiator for causing said signals to be substantially simultaneously focused on or through said target; and
    a detector for acquiring spectral information reflected from said target and coupled to a second pulsed optical beam derived from said laser for generating an electrical signal representative of some characteristic of the target.

2. An apparatus as in claim 1, wherein said detector includes a second photoconductive switch activated by a pulsed laser beam derived from said laser and having the frequency spectrum f+Δf, 2(f+Δf), 3(f+Δf), ... etc., where Δf is of the order of 2.5 KHz.

3. An apparatus as defined in claim 1, further comprising a processor coupled to said detector for analyzing said electrical signal and determining a characteristic of said target based upon the absorption characteristics of said target in the 100 GHz to over 2 THz frequency band.

4. An apparatus as defined in claim 1 wherein said laser is a mode-locked laser for generating the respective pulsed laser beams directed to the first photoconductive switch.

5. An apparatus as defined in claim 4, wherein the output of the laser is split into two paths, the first path coupled to the first photoconductive switch, and the second path coupled to a beam modifying component.

6. An apparatus as defined in claim 5, wherein the output of said beam modifying component is coupled to said detector.

7. An apparatus as defined in claim 5, wherein said beam modifying component is a dispersive phase modulator.

8. An apparatus as defined in claim 7, wherein said dispersive phase modulator produces an output signal with a sequence of frequency shifted components with respect to the pulsed laser beam with each frequency shift in said sequence increasing with increasing optical frequency.

9. An apparatus as defined in claim 7, wherein said dispersive phase modulator is a lithium niobate modulator with the pulse intensity of the input pulse adjusted so as to adjust the dispersion in the non-linear lithium niobate medium.

10. An apparatus as in claim 1 wherein the source of pulsed signals in the range of frequencies further comprises hundreds of locked modes spanning more than 1000 GHz.

11. An apparatus for analyzing, identifying or imaging a target, comprising:
a source of pulse signals in the range of frequencies of from 100 GHz to 3 THz;
a radiator for causing said signals to be substantially simultaneously focused or through said target;
a detector including a photoconductive switch activated by a pulsed laser beam with the frequency spectrum $f+\Delta f$, $2(f+\Delta f)$, $3(f+\Delta f)$, ... etc. where f is the order of 100 MHz and $\Delta f$ is of the order of 2.5 KHz, for acquiring spectral information reflected from or transmitted through said target for generating an electrical signal representative of some characteristics of the target; and
means coupled to said detector for processing said electrical signal.

12. An apparatus as defined in claim 11, further comprising a processor coupled to said detector for analyzing said electrical signal and determining a characteristic of said target based upon the absorption characteristics of said target in the 100 GHz to over 2 TH frequency band.

13. An apparatus as defined in claim 11, further comprising:
a mode-locked laser for generating a pulsed laser beam wherein the output of the laser is split into two paths, the first path coupled to the source of pulse signals in the range 100 GHz to over 2 THz, and the second path coupled to a beam modifying component having an output coupled to the detector.

14. An apparatus as in claim 11 wherein the pulsed beam further comprises hundreds of locked modes spanning more than 1000 GHz.

15. A portable apparatus for analyzing, identifying or imaging a target, comprising:
a housing capable of being supported by a user;
a source of pulse signals in said housing including a single mode-locked laser, said signals having simultaneous respective frequencies of f, 2f, 3f, ... etc. where f is the order of 100 MHz and said signals being in the range of frequencies from 100 GHz to over 2 THz;
a radiator coupled to said source of pulsed signals for causing said signals to be focused on said target;
a detector in said housing for acquiring spectral information reflected from or transmitted through said target and generating an electrical signal representative of some characteristics of the target; and
a processor in said housing coupled to said detector for processing said electrical signal.

16. An apparatus as in claim 15 wherein the source of pulsed signals further comprises hundreds of locked modes spanning more than 1000 GHz.

17. A transceiver comprising:
a mode-locked laser for generating a pulsed laser beam;
a beam splitter for splitting said beam into first and second optical beams;
a photoconductive switch activated by said first optical beam resulting in a frequency spectrum f, 2f, 3f, ... etc. where f is the order of 100 MHz; and
a detector including a photoconductive switch activated by said second optical beam with the frequency spectrum $f+\Delta f$, $2(f+\Delta f)$, $3(f+\Delta f)$, ... etc. where $\Delta f$ is of the order of 2.5 KHz, for acquiring spectral information reflected from or transmitted through said target and coupled to source for generating an electrical signal representative of some characteristics of the target.

18. An apparatus as in claim 17 wherein the first optical beam further comprises hundreds of locked modes spanning more than 1000 GHz.

19. A method of identifying or imaging a target comprising:
providing a single mode-locked laser for generating a pulsed laser beam;
simultaneously transmitting a predetermined spectral pattern of pulse signals derived from said pulsed laser beam to a target, said signals having respective frequencies of f, 2f, 3f, ... etc. where f is the order of 100 MHz and said signals being in the range of frequencies from 100 GHz to over 2 THz;
detecting the return signals in said frequency range after transmission through or reflection from said target by utilizing a detector tuned to said spectral pattern derived from said pulsed laser beam shifted by a sequence of non-identical small amounts from said spectral pattern; and
analyzing said spectral information to identify said target or a compositional characteristic thereof.

20. A method as defined in claim 19, further comprising driving said detector by a dispersive phase modulator.

21. A method as defined in claim 19, further comprising driving said dispersive phase modulator by a sawtooth generator and said pulsed laser beam.

22. A method as defined in claim 19, wherein said pulsed laser beam activates a photoconductive switch resulting in a frequency spectrum f, 2f, 3, ... etc. where f is the order of 100 MHz.

23. A method as defined in claim 19, wherein said pulsed laser beam is applied to and acted upon by a dispersive phase modulator.

24. A method as defined in claim 19, wherein said pulsed laser beam is split into two parts, with one part activating a photoconductive switch, and a second part being applied to and acted upon by a dispersive phase modulator.

25. A method as defined in claim 24, wherein the output of the dispersive phase modulator is coupled to said detector.

26. A method as defined in claim 19, wherein said detector is activated by a pulsed optical beam with the frequency spectrum $f+\Delta f$, $2(f+\Delta f)$, $3(f+\Delta f)$, ... etc. where $\Delta f$ is of the order of 2.5 KHz.

27. A method as defined in claim 19, wherein said detecting step provides instantaneous multi-spectral heterodyne down conversion of said return signals.

28. An apparatus as in claim 19 wherein the predetermined spectral pattern of pulse signals further comprises hundreds of locked modes spanning more than 1000 GHz.

* * * * *